United States Patent
Muto et al.

(10) Patent No.: US 6,453,729 B1
(45) Date of Patent: Sep. 24, 2002

(54) SURFACE SHAPE EVALUATION METHOD AND DEVICE FOR SPHERICAL BODY

(75) Inventors: Yasushi Muto; Banda Noda, both of Fujisawa (JP)

(73) Assignee: NSK Ltd., Tokyo (JP)

( * ) Notice: Subject to any disclaimer, the term of this patent is extended or adjusted under 35 U.S.C. 154(b) by 0 days.

(21) Appl. No.: 09/667,071

(22) Filed: Sep. 21, 2000

(30) Foreign Application Priority Data

Sep. 21, 1999 (JP) .......................................... 11-267650

(51) Int. Cl.[7] .......................... G01B 17/06; G01H 17/00
(52) U.S. Cl. ........................................ 73/104; 33/517
(58) Field of Search ...................... 73/104, 105; 33/517

(56) References Cited

U.S. PATENT DOCUMENTS

| | | | | |
|---|---|---|---|---|
| 2,821,023 A | * | 1/1958 | Mims ........................... | 33/517 |
| 3,106,837 A | * | 10/1963 | Plumb et al. ................. | 33/517 |
| 3,468,034 A | * | 9/1969 | Blinder ........................ | 33/517 |
| 6,250,142 B1 | * | 6/2001 | Goransson ................... | 73/105 |

FOREIGN PATENT DOCUMENTS

| | | | | |
|---|---|---|---|---|
| DE | 2742326 | * | 3/1979 | ................. 73/104 |
| JP | 6-58849 | | 9/1994 | ................. 73/104 |
| JP | 8-247151 | | 9/1996 | ................. 384/450 |
| SU | 1193475 | * | 11/1985 | ................. 73/104 |
| SU | 1262343 | * | 10/1986 | ................. 73/104 |

* cited by examiner

Primary Examiner—Daniel S. Larkin
(74) Attorney, Agent, or Firm—Crowell & Moring LLP (57) ABSTRACT

A surface shape evaluation method for a spherical body comprising the steps of: providing a support hole having a smaller diameter than the spherical body and having a curved bearing surface formed on its opening to have a curvature substantially equal to the curvature of the surface of the spherical body, providing a rotation drive arm for transmitting only a rotation component to the spherical body, providing a vibration sensor having a probe with a flat tip end, rotating the spherical body on a predetermined center axis and on the opening, such that one portion in the radial direction of the spherical body comes into contact with the curved bearing surface while the portion opposite to the one portion in the radial direction of the spherical body comes into contact with the tip end of the rotation drive arm, abutting the flat tip end of the probe of the vibration sensor to a surface portion of the spherical body located on a hypothetical flat surface which is orthogonal to the center axis and passes through the central point of the spherical body to detect the surface shape from the surface portion as vibration amounts, from which the results are through a sampling process and an adding and averaging process in harmonization with rotation velocity of the spherical body, and a frequency analysis process are evaluated as a numerical value e.g. of at least displacement.

2 Claims, 9 Drawing Sheets

SURFACE SHAPE EVALUATION METHOD AND DEVICE FOR SPHERICAL BODY

FIELD OF THE INVENTION

The present invention relates to a surface shape evaluation method and device for a spherical body, which is used for judgement, good or not, of the surface shape of a ball for incorporation in a ball bearing for use in a rotation support portion of e.g. a hard disc drive device (HDD) or video tape recorder (VTR).

BACKGROUND OF THE INVENTION

Figure 9:
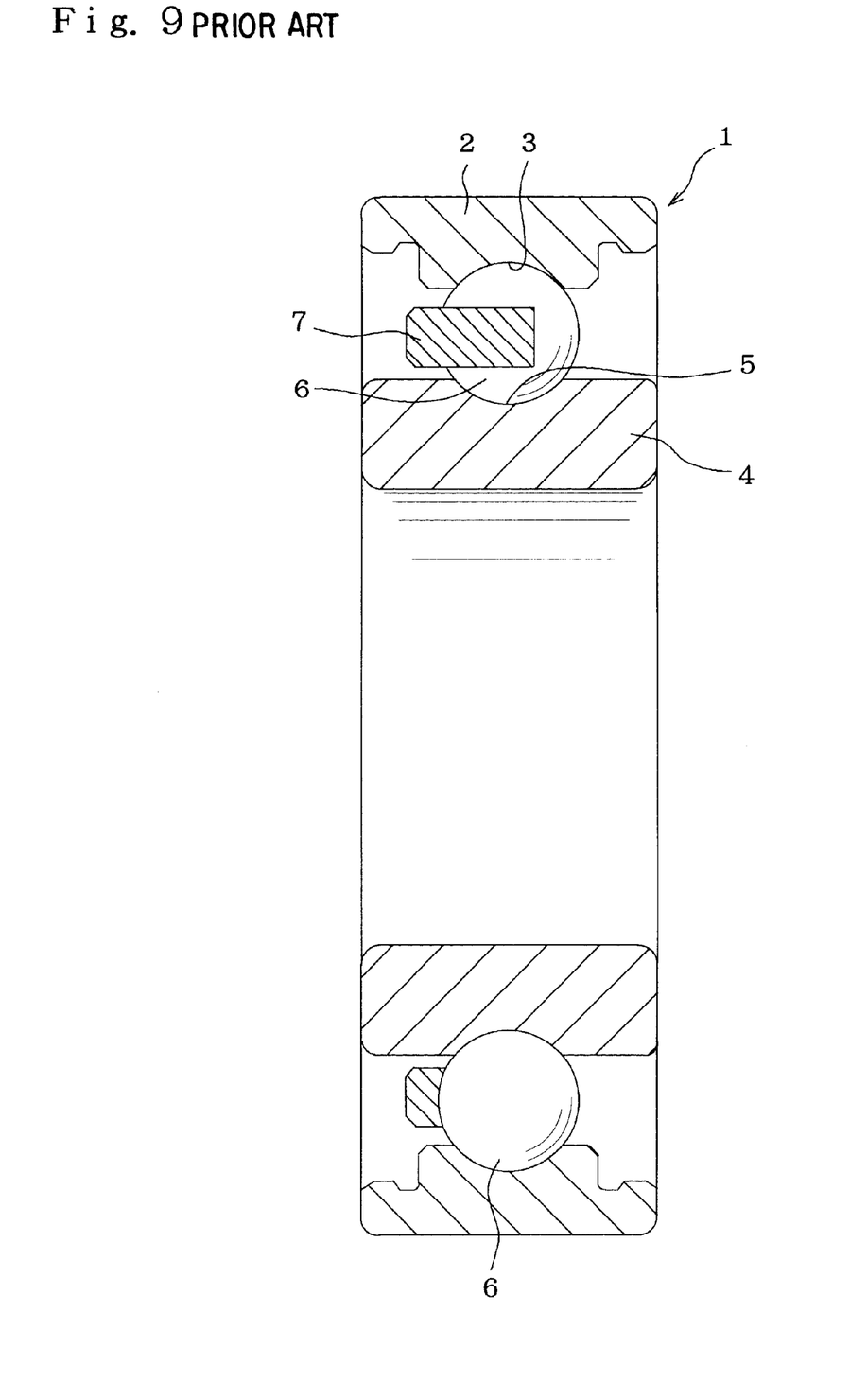
FIG. 9 is an enlarged view of an example of the ball bearing having balls incorporated therein and evaluated by the present invention.

Used in the hard drive device (HDD) or video tape recorder (VTR) is a ball bearing 1 as shown in FIG. 9, which comprises an outer ring 2 having an inner peripheral surface formed with an outer ring raceway 3, an inner ring 4 having an outer peripheral surface formed with an inner ring raceway 5, a plurality of balls 6 rotatably provided between the outer and inner ring raceways 3, 5 and held in a cage 7, so that the outer ring 2 and inner ring 4 are rotated relative to each other.

Figure 10:
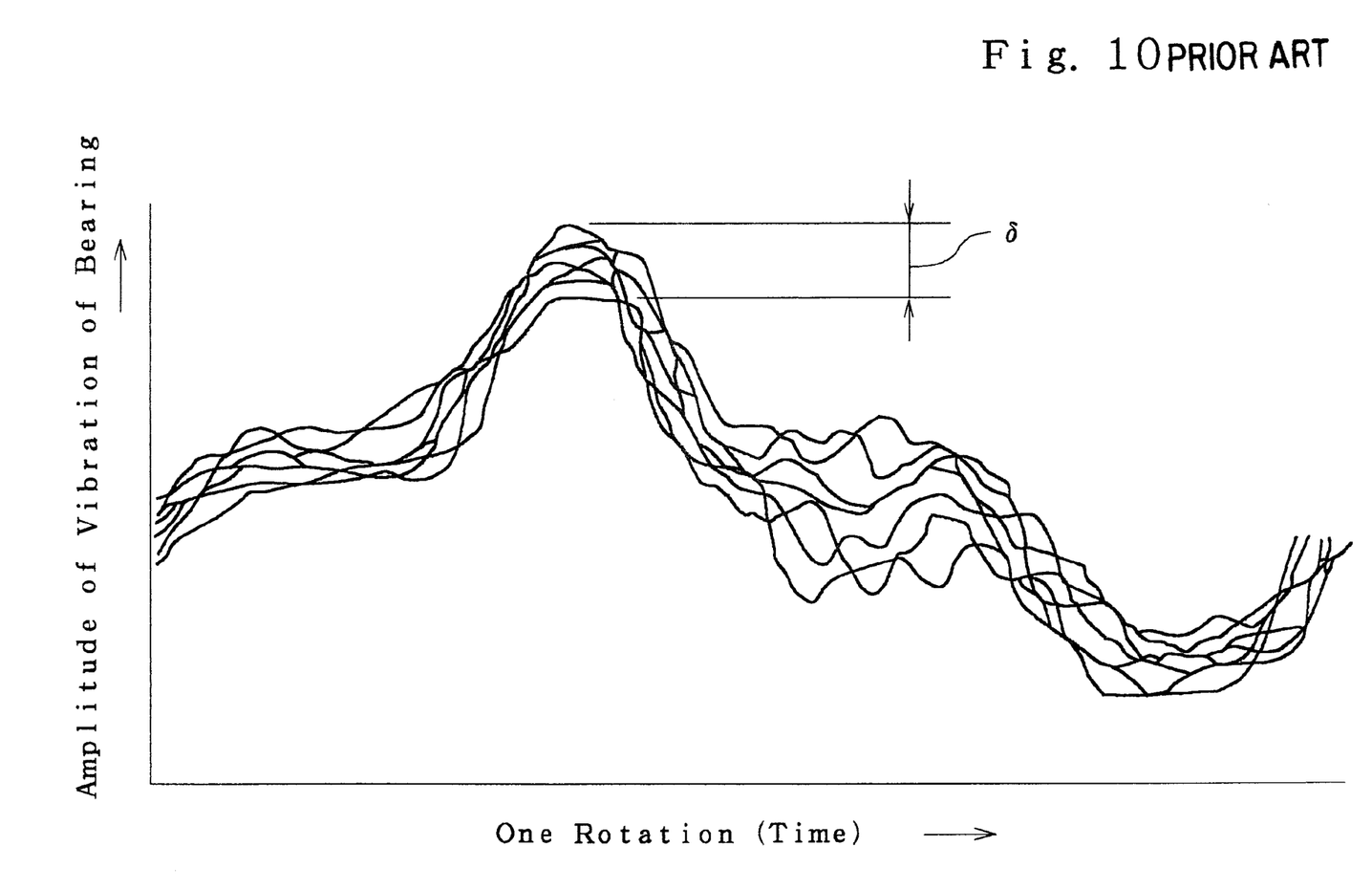
FIG. 10 is a diagram showing the vibration characteristics of a ball bearing.

The ball bearing 1 for use in the hard disc drive device (HDD) or video tape recorder (VTR) must be provided with extremely high rotation precision. For example, in the case of the ball bearing 1 to be incorporated in the motor However, there are minute lands and recesses (undulation) on the rolling surface of the balls 6 for use in the ball bearing 1, which could not be avoided in processing. And, the distance between the outer ring raceway 3 and the inner ring raceway 5 corresponding to the diameter of the balls 6 changes slightly during a single rotation of the balls due to undulation. As a result, the positional relationship of the inner ring 3 with respect to the outer ring 1, and vice versa, changes slightly as shown by the curved lines in FIG. 10. This is referred to as runout. Incidentally, the displacement appearing in the ordinate in FIG. 10 is the vibration amplitude of the ball bearing 1. This runout is repeated every rotation of the inner ring 4 (or of the outer ring 2). In addition, the amount (displacement amount) and location of runout slightly changes, which is so-called non-repetitive run out (NRRO). In other words, the relation in location between the outer ring 2 and the inner ring 4 is not reproduced and vibrations caused change from rotation to rotation. Consequently, as the integrity of information on the magnetic disc becomes high, errors can be produced in reading and weighting by the magnetic head. Therefore, the performance of the ball bearing 1 is a bar against the high density of the HDD.

Accordingly, the non-repetitive runout of the ball bearing 1 must be minimized to obtain a high density HDD. The roundness of the balls 6 must be improved to make the waviness of the rolling surface of the balls 6 small so as to minimize the non-repetitive runout. On the other hand, it is substantially impossible on technology to further improve the process precision of the balls 6, and therefore to minimize the non-repetitive runout by improving the roundness of the balls 6. Even if it is possible to further improve the roundness, it will be costly, resulting in high production cost of the ball bearing 1 having the balls 6 incorporated therein, and of the HDD having the ball bearing 1 incorporated therein.

Under such a situation, a ball bearing with small non-repetitive runout is disclosed in JP Patent Publication Toku Kai Hei 8-24715 where the roundness of the balls 6 is not particularly improved. The ball bearing disclosed in the publication is provided with one of the following conditions:

1. With the components of the number of waves per circumference on the rolling surface of the ball 6, the sum of the even orders of waviness is smaller than the sum of the odd number of waviness.

2. With the components of the number of waves per circumference on the rolling surface of the ball 6, the maximum in half amplitude of the even orders of waviness is smaller than the maximum in half amplitude of the odd orders of waviness.

3. With the components of the number of waves per circumference on the rolling surface of the ball 6, the sum of the even orders of waviness is smaller than the sum of the odd orders of waviness, and in addition the maximum in half amplitude of the even orders of waviness is smaller than the maximum in half amplitude of the odd orders of waviness.

With the rolling surface of the balls 6 in the ball bearing disclosed in Toku Kai Hei 8-247151, the non-repetitive runout can be made small because the sum of the even orders of waviness and the maximum in half amplitude of the even orders of waviness having larger bad effects on the vibration characteristics are smaller than the sum of the odd orders of waviness and the maximum in half amplitude of the odd orders of waviness, respectively. The sum of the odd orders of waviness and the maximum in half amplitude of the odd orders of waviness are not necessarily made smaller than in the prior art because the do not badly affect the vibration characteristics. Therefore, even if the roundness of the balls is not particularly improved, the vibration characteristics are improved and non-repetitive runout can be made small. Toku Kai Hei 8-247151 is incorporated in this specification by reference, which describes the reasons of the improvement in vibration characteristics achieved, by making small the sum of the even orders of waviness and the maximum in half amplitude of the even orders of waviness even if the sum of the odd orders of waviness and the maximum in half amplitude of the odd orders of waviness are not necessarily made small.

The invention as shown in Toku Kai Hei 8-247151 can realize a ball bearing and HDD, etc., with higher performance and lower cost. However, it is necessary to efficiently judge the shape of the rolling surface of the balls 6 produced whether it conforms to the conditions described in the publication.

Conventionally, a general shape measurement device is used for judgement, good or not, of the rolling surface of the balls 6, where the error in rotation of the spindle to rotate the balls 6 to be detected is directly associated with the measurement error. In addition, in the worst case, the rotation error may be larger than the components of waviness. Accordingly, the rotation precision of the spindle must be sufficiently made larger, so that the production cost of the measurement device is unavoidably increased. On the other hand, with the waviness measurement devices available in the market, it is difficult to secure the rotation precision, and specifically to precisely evaluate the low frequency components of the surface shape, and in addition wear the bearing portions for the ball is severe, so that rotation of the ball is unstable, and precise measurement is difficult, and reproductivity is difficult in measurement.

In the prior art devices, the waviness of the rolling surface of the balls is evaluated by summing the components of waviness which have passed stationary filters having appropriate band-pass frequency ranges. Accordingly, it is impossible to evaluate specific components of waviness badly affecting the vibration characteristics of the ball bearing. For example, ball bearings having larger odd orders of waviness are rejected as poor even when its even orders of waviness are small. Therefore, it is impossible to evaluate the balls 6 for the ball bearing which must be optimum for the characteristics of the instruments such as HDDs where the ball bearing is incorporated.

In addition, the conventional measurement devices have a probe the tip end of which is sharp or of a spherical convex shape, so that it is difficult to locate the tip end of the probe in alignment with the portion to be detected for evaluation of tiny balls 6. Specifically, in measurement of the waviness of the rolling surface of the ball 6, the tip end of the probe is abutted to a so-called equator portion of the ball 6 during rotation. The equator portion of the ball 6 is located on the hypothetical surface which passes through the central point of the ball 6 and is orthogonal to the center axis of rotation. This operation is inconvenient for tiny balls 6 and takes a long time.

SUMMARY OF THE INVENTION

It is an objective of the present invention to provide a surface shape evaluation method and device for a spherical body, wherein the spherical body is rotated on a predetermined central axis, and the measurement of shape is conducted at a surface portion of the spherical body located on the hypothetical surface which passes through the central point of the ball 6 and is orthogonal to the center axis of rotation, for judgement, good or not, of the spherical body.

It is another objective of the present invention to provide a surface shape evaluation method and device for a spherical body, wherein the surface shape affecting the performance of the vibration and sound of the ball bearing is highly precisely measured without being affected by the rotation precision of the rotation drive portion of it for reliable evaluation and easy measurement operation.

It is another objective of the present invention to provide a surface shape evaluation method and device for a spherical body, whereby an inexpensive ball bearing with high performance in vibration and sound can be realized for efficient development of such a ball bearing.

DETAILED DESCRIPTION OF PREFERRED EMBODIMENTS

Figure 2:
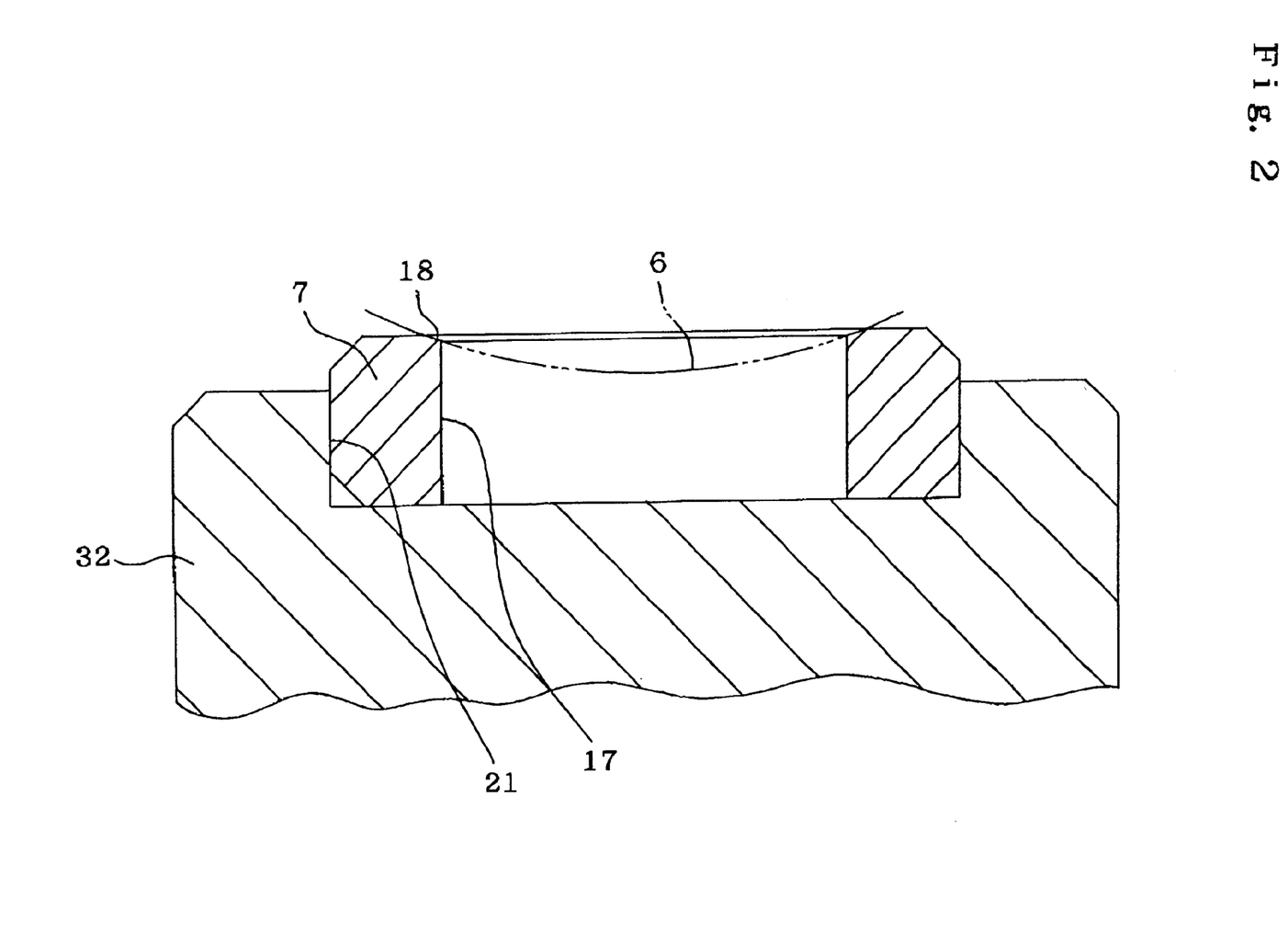
FIG. 2 is an enlarged view of Portion II in FIG. 3 with the ball omitted.
Figure 3:
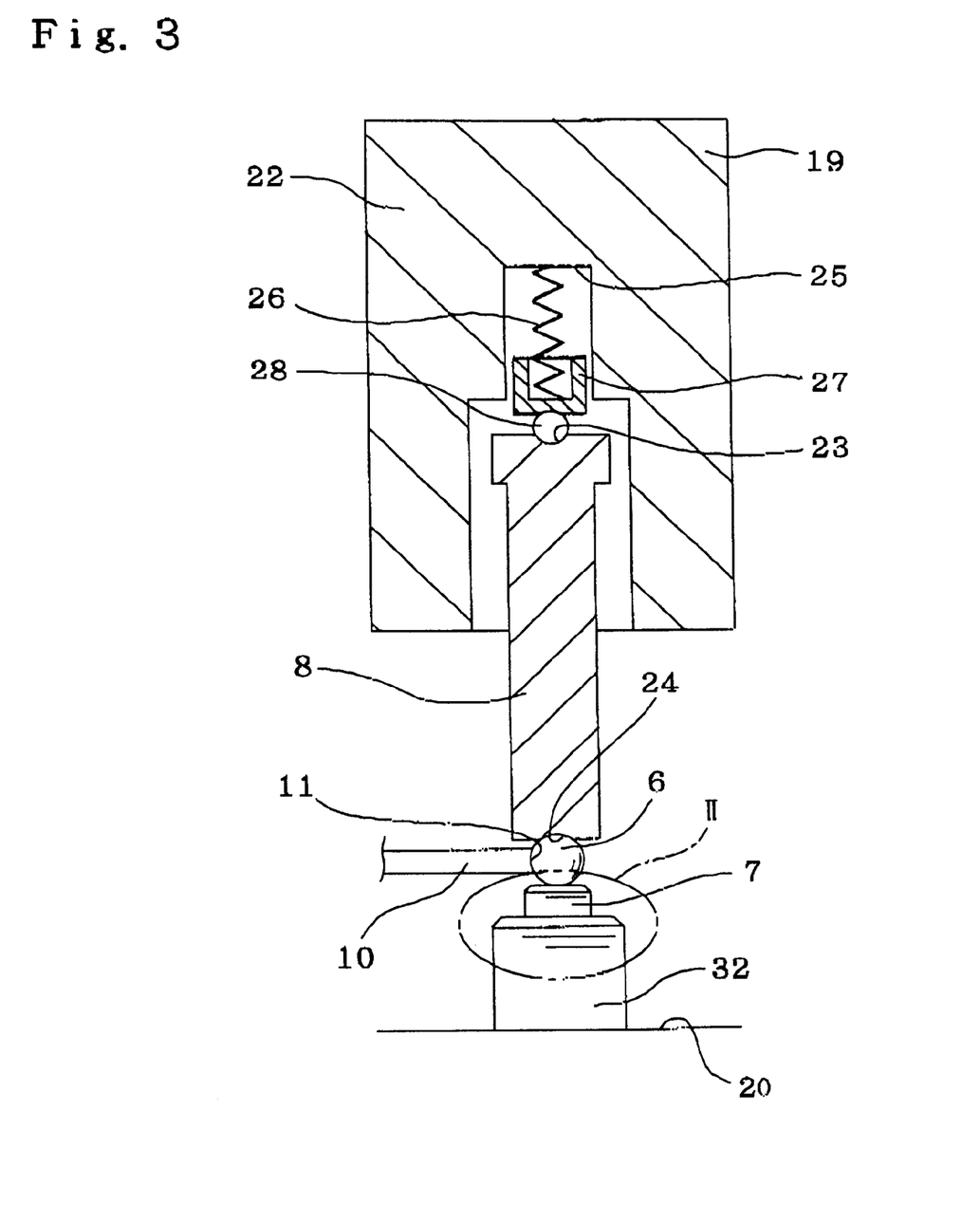
FIG. 3 is a vertical cross sectional view of an example of the drive apparatus to rotate the ball.

Now, some preferred examples are explained referring to the drawings. The ball 6, which is an object to be detected, is guided on the rotation guide tool 7, as shown in FIG. 2, by way of a drive means with its center on the vertical line. In this state, the ball 6 is rotated and driven by a drive arm 8, as shown in FIG. 3, which is a rotation drive means having a centering function.

Figure 1:
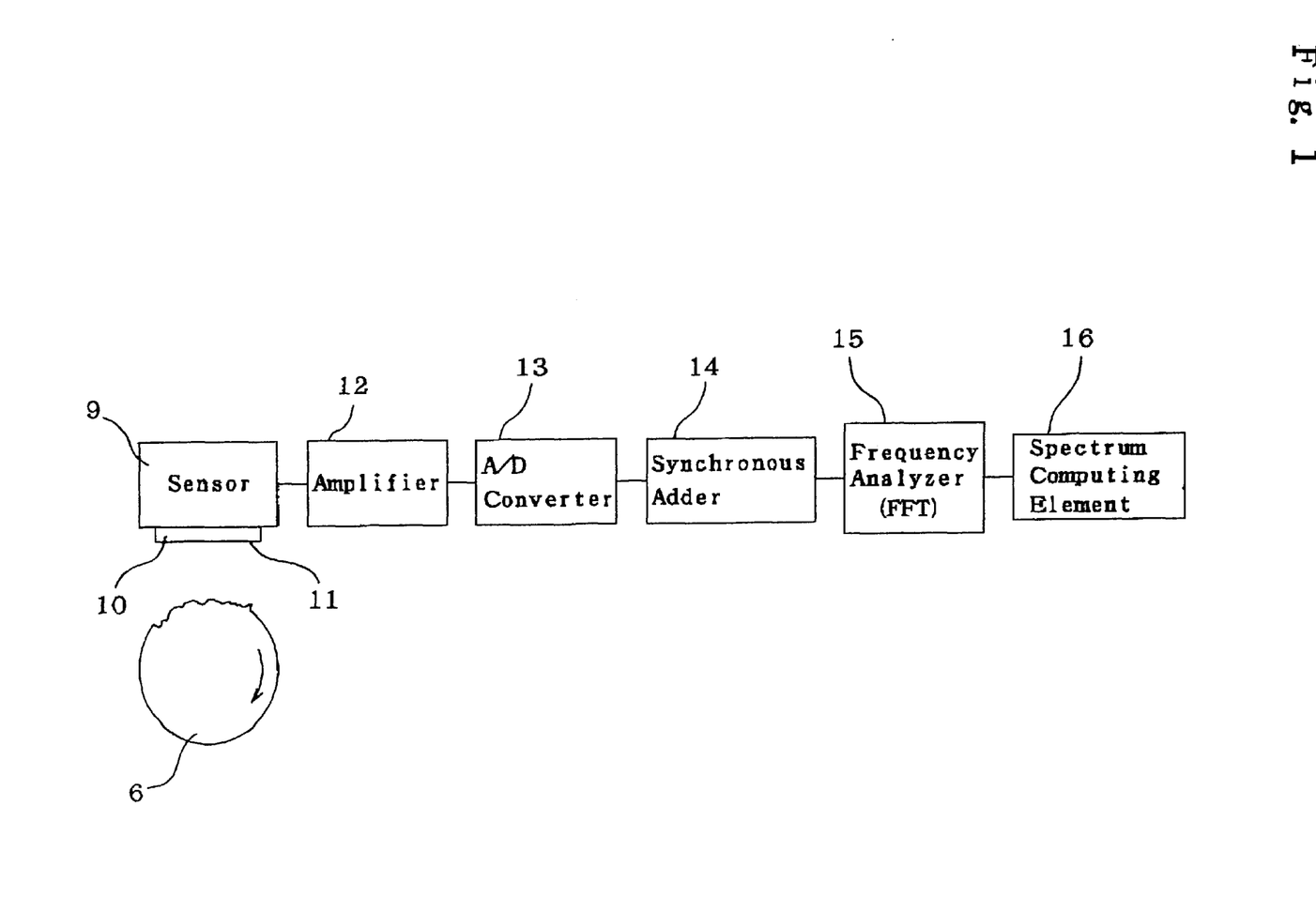
FIG. 1 is a block diagram showing an example of the embodiment of the surface shape evaluation method and device for a spherical body according to the present invention.

A sensor 9, which is a vibration sensor of the velocity type, is provided on one side of the ball 6, and has a probe 10 engaged with part of the rolling surface of the ball 6. The probe 10 has a center axis which is located on the horizontal line passing through the center of the ball 6. In addition, the probe 10 has a tip end surface 11 which is flat and orthogonal to the center axis of the probe 10. The tip end surface 11 comes in contact with the equator portion of the rolling surface of the ball 6, which is the portion located on the hypothetical horizontal surface passing through the center of the ball 6. In this state, when the ball 6 is rotated on the vertical axis, the probe 10 moves back and forth in the horizontal direction whereby the surface shape of the equator portion is detected as a vibration amount.

Incidentally, since the tip end surface 11 is flat, when the surface shape of the rolling surface has minute lands and recesses, the tip end surface 11 can detect the peak of the nearby lands. Specifically, a portion adjacent the point which the center of the tip end surface 11 faces projects largely from the point, the probe 10 is axially displaced corresponding to the portion adjacent the point. Accordingly, the equator portion is easily positioned by adopting the above-mentioned shape of the tip end surface 11, and it is possible to precisely measure the surface shape which is practically useful.

Incidentally, when the ball 6 is incorporated in the ball bearing, the contact condition where the rolling surface of the ball 6 comes into contact with the outer ring raceway 3 and the inner ring raceway 5 in the bearing is changed by the nearby lands. Accordingly, the fact that the tip end surface 11 can detect the peak of the nearby lands is desirable because it is based on the measurement condition which corresponds to the condition where the ball 6 is actually incorporated in the ball bearing.

The detection signals from the sensor 9 are amplified by the amplifier 12 and then sent to the A/D converter 13. With the A/D converter 13, the analog signals representing the vibration amount sent from the sensor 9 through the amplifier 13 are converted digital signals for output.

Thus, the digital signals representing the vibration amount sent from the A/D converter 13 are synchronously added together in the synchronous adder 14, where the sampling of the characteristic values is carried out in the state where the characteristic values are synchronous with the rotation velocity of the ball based on the drive arm 8. The values obtained through the sampling are added together to obtain the average. The rotation of the ball 6 is conducted several times, and the vibration amount is obtained for each rotation, and the vibration amounts for respective rotations are added together and the sum is divided by the number of rotations (the number of samplings) to obtain the average.

The average of the vibration amounts obtained as mentioned above is sent to the frequency analyzer 15 and then to the spectrum computing element 16, which form a decision means. With the frequency analyzer 15, the average of the vibration amounts sent from the A/D converter 13 is subjected to the frequency analysis through Fourier transform (FFT), and the resulting value is sent to the spectrum computing element 16. At this time, the vibration value is converted to at least one of the characteristic values of displacement, velocity, and acceleration that is to a single characteristic value, two characteristic values, or three whole characteristic values. Based on the characteristic value(s), spectrum computing is carried out on the desired components (the operator can freely set) of a number of waves at the spectrum computing element 16. Specifically, as shown in Japanese Patent publication Toku Kai Hei 8-247151, the undulation in the rolling surface of the ball 6 has various components of a number of waves per circumference, and the components of the number of waves per circumference differently affect the ball bearing in which the ball 6 is incorporated. For example, the component of even orders of waviness largely affects non-repetitive runout than the component of odd orders of waviness. Accordingly, with the spectrum computing element 16, the waviness on the equator portion of the rolling surface of the ball 6 is obtained with respect to a set number of waves, and the resulting data are displayed on the display means (not shown), such as CRT, printer. The operator can evaluate the ball 6 from the output on the display means.

On the other hand, the rotation guide tool 7 for rotatably supporting the ball 6 on the vertical axis is formed in a generally annular shape, as shown in FIG. 2, and with a support hole 17 with a small diameter at its center. Formed on the peripheral edge of the opening at the upper end of the support hole 17 by way of lapping is a curved bearing surface 18 which is a spherical concave surface having a curvature substantially equal to (equal to or slightly larger than) the curvature of the rolling surface of the ball 6. With the rotation guide tool 7, at least the curved bearing surface 18 is made of a material having a high hardness and a low friction coefficient. Accordingly, the rotation guide tool 7 is generally made of ruby, or the rotation guide tool 7 has a main body which is made of an iron-based metal or alloy, and the surface portion at the curved bearing surface 18 on the main body is coated with a thin film of synthetic diamond. This thin film of synthetic diamond can be formed using, for example, a CVD (chemical vapor deposition) process.

An evaluation device of the present invention is shown in FIG. 3, where the rotation guide tool 7 is supported by a drive apparatus 19 for rotating the ball 6 on the vertical axis such that the center axis of the rotation guide tool 7 is vertically directed. Specifically, fixed on the base plate 20 of the drive apparatus 19 is a support member 32 on the upper surface of which a circular concave portion 21 is formed. Then, the rotation guide tool 7 is fixedly fitted into the circular concave portion 21 making the displacement impossible in the radial (horizontal) direction. In this state, the ball 6 is put on the curved bearing surface 18, so that the ball 6 is rotatable with a light force on the vertical axis.

The drive arm 8 is vertically provided above the rotation guide tool 7. With the drive arm 8 vertically arranged, only the rotation component of the spindle 22 rotatingly driven by the power source such as an electric motor (not shown) is seen by the ball 6. In other words, the drive arm 8 has a centering function to transmit only the rotation component of the drive force of the spindle 22 to the ball 6, removing the whirling component in the radial direction.

In the present example, the upper and lower end surfaces of the drive arm 8 are formed with conical engagement recesses 23, 24 at the central portion thereof, respectively. The conical engagement recess 24 formed on the lower end surface comes into contact with the upper end, the radially opposite end, of the ball 6. On the other hand, the central portion of the lower end of the spindle 22 is formed with a hole 25 which is open in the lower end surface of the spindle 22. Provided between the innermost end surface of the hole 25 and the drive arm 8 are, from the side of the innermost end surface, a compression coil spring 26, a spacer 27, and a center ball 28 in series. The lower end portion of the center ball 28 is fitted into the engagement recess 23 formed on the upper end surface of the drive arm 8.

As the spindle 22 is rotated for measurement of the shape of the rolling surface of the ball 6, this rotation is transmitted to the ball 6 through the compression coil spring 26, spacer 27, centering ball 28, and drive arm 28. The friction force at the engagement portion between the lower end of the rolling surface of the ball 6 and the curved bearing surface 18 is outstandingly smaller than those at the engagement portions between the innermost end surface of the hole 25 and the upper end of the compression coil spring 26, between the lower end of the compression coil spring 26 and the upper surface of the spacer 27, between the lower surface of the spacer 27 and the upper end of the centering ball 28 and between the lower end of the centering ball 28 and the concave portion 23. In addition, the rigidity of the compression coil spring 26 in the torsion rotation direction is substantially larger than the friction force at the engagement portion between the lower end of the rolling surface of the ball 6 and the curved bearing surface 18.

Accordingly, the rotation component of the spindle 22, in which there is no displacement in phase with respect to the rotation direction, is transmitted, as it is, to the ball 6 to rotate the ball 6 on the vertical axis. In addition, even if the spindle 22 shakes in the radial direction, this shaking is absorbed by the relative displacement in the radial direction between the spindle 22 and the drive arm 8 so as not to be transmitted to the ball 6. In addition, when the spindle 22 shakes in the axial direction, this is absorbed by the compression coil spring 26, specifically its compression and expansion. Accordingly, upon measurement of the shape of the rolling surface of the ball 6, the ball 6 is rotated on the vertical axis without shaking in any direction.

With the surface shape evaluation device of the spherical body according to the present invention constructed as mentioned above, the surface shape of the rolling surface of the ball 6, which affects the performance with respect to the vibration and sound of the ball bearing can precisely measured without being affected by the precision on rotation of the spindle 22 which is a rotation drive portion, resulting in a reliable evaluation. In addition, the operation for measurement is easy in the present invention.

Since the rotation drive means having centering function is operated to rotate the ball 6 rotatably supported by the curved bearing surface 18 of the rotation guide tool 7, the ball 6 can be rotated with a high precision. In other words, the ball 6 does not whirl and simply rotate on the vertical axis, so that the shape component such as waviness on the rolling surface of the ball 6 can be precisely measured.

In this example, the curved bearing surface 18 is made of a hard material with low friction coefficient such as synthetic ruby or synthetic diamond, and therefore it is possible to achieve highly precise and stable measurement for a long time of period substantially without wearing in the curved bearing surface 18.

Figure 4:
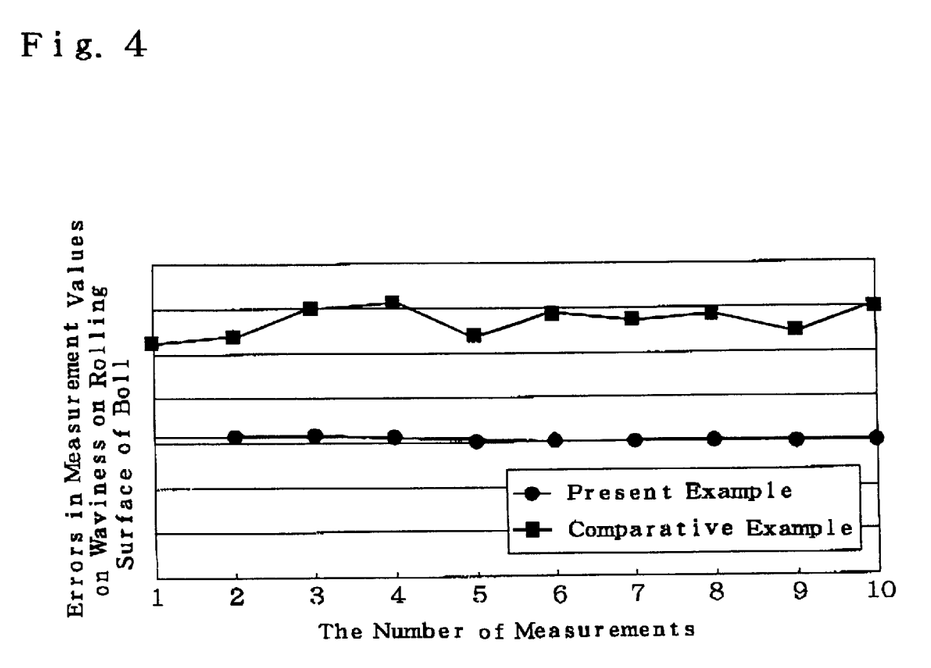
FIG. 4 is a graph showing a result of the experiment to know the effects of the material and shape of the rotation guide tool on the measurement results.

FIG. 4 shows a result of experiments the inventors conducted with respect to this point. In the experiments, the curved bearing surface 18 of the rotation guide tool 7 for an example of the present invention which is made of synthetic ruby is compared with a rotation guide tool which is made of copper, a relatively soft metal, and formed in a simple annular shape having a sharp edge along the opening in contact with the rolling surface of the ball 6 for a comparison example. With the conditions except for the rotation guide tool being the same to each other, e.g. using the same ball 6, the operation for measurement of shape precision with respect to the rolling surface of the ball 6 was repeated ten times for each example.

FIG. 4 shows the results of the experiment comparing the present example with the comparative example, where the ordinate represents the errors in the measurement values of waviness on the rolling surface of the ball 6 while the abscissa represents the number of measurements. As clear from the results of the experiment in FIG. 4, with the curved bearing surface 18 of the rotating guide tool 7 coated with hard and low friction material, the precision in shape measurement on the rolling surface of the ball 6 is outstandingly improved.

Since the tip end surface 11 of the probe 10 of the sensor 9 is flat, the operation to abut the tip end surface 11 to a portion of the ball 6 on the hypothetical flat surface (the horizontal surface containing the center of the ball 6) which is orthogonal to the vertical axis, that is the center axis of rotation, and passes through the center of the ball 6 is easy. In addition, the contact surface pressure at the engagement portion between the tip end surface 11 of the probe 10 and the equator portion on the rolling surface of the ball 6 is just small, the tip end surface 11 is substantially prevented from being worn, and the endurance of the probe 10 is improved. With the tip end surface 11 being flat, the surface shape of the equator portion of the ball 6, practically useful, can be precisely measured, which desirably simulates the measurement condition where the ball 6 is actually incorporated in the ball bearing.

In the present invention, the synchronous adder 14 is used to obtain the average of values representing the vibration amount through sampling and adding in synchronizing with the rotation velocity of the ball 6 due to the drive apparatus 19, and therefore the effect of the deviation in rotation of the ball 6 is minimized, resulting in measurement with a high SN ratio. It is possible to minimize the deviation in rotation (whirling in the horizontal direction of the vertical axis that is the rotation center) of the ball 6 during measurement operation using the drive apparatus 19, but impossible to completely remove it. Therefore, in this invention, the ball 6 is rotated several times (the more the better), the measurement values in the same phase with respect to the rotation direction are added, and the resulting value is divided by the number of additions to obtain the average of the measurement results, thus removing the effects of the deviation in rotation and improving the SN ratio.

The signal for representing the vibration amount with the SN ratio improved is input into the frequency analyzer 15 where the intensity is subjected to differential or integral calculus. Through such operation, the shape of the rolling surface of the ball 6 can be converted for evaluation to a characteristic value such as displacement, velocity, acceleration, and the evaluation of the surface shape of the ball 6 is made flexible. Specifically, the surfaced shape can be evaluated with a single measurement operation based on any characteristic value such as displacement, velocity, acceleration. For example, the displacement which is related to non-repetitive runout (NRRO) is important for evaluation of the surface shape because it corresponds to the whirling of the ball bearing having the ball 6 incorporated therein. And, the velocity related to the Anderon Value and acceleration related to the G value are important for evaluation of the surface shape because they correspond to the radial or axial vibration of the ball bearing having the ball 6 incorporated therein.

Manufacturers of the ball bearing are required by users of the ball bearing (HDD manufacturers etc.) to reduce the radial or axial vibration at the predetermined frequency for example to prevent the resonance of the housing etc.

On the other hand, with the waviness of the rolling surface of the ball 6 which is not of the bearing parts, the relation between the number of waves and the frequency of the vibration is known in the art as shown in Table 1. Therefore, the waviness is made small with respect to the number of waves corresponding to the frequency required to reduce the vibration at the frequency.

TABLE 1

| vibration-direction waviness | radial direction, angular-direction | | axial direction | |
| --- | --- | --- | --- | --- |
| | number of waves in waviness | frequency of vibration-produced | number of waves in waviness | frequency of vibration-produced |
| | 2n | $2nf_b \pm f_c$ | 2n | $2nf_b$ | n: positive integer,
$f_b$: rotation frequency of ball (Hz),
$f_c$: rotation frequency of cage (Hz)

With the present invention, the displacement, velocity, and acceleration are evaluated independently or associated with each other, and therefore it is easy to correspond to the situation as mentioned above. Specifically, when corresponding to the requirement as mentioned above, it is acceptable that the waviness (the displacement of the rolling surface in the radial direction) is finally made small, but if the number of waves is large, it is not always possible to identify the existence of waviness from the vibration amount detected by the sensor 9. In such a case, it is possible to detect the existence of waviness from the velocity or acceleration of the vibration appearing based on the existence of waviness. Accordingly, it is possible to identify the existence of waviness with a specified number of waves by observing the characteristic value which is the clearest among the displacement, velocity, and acceleration.

Figure 5A:
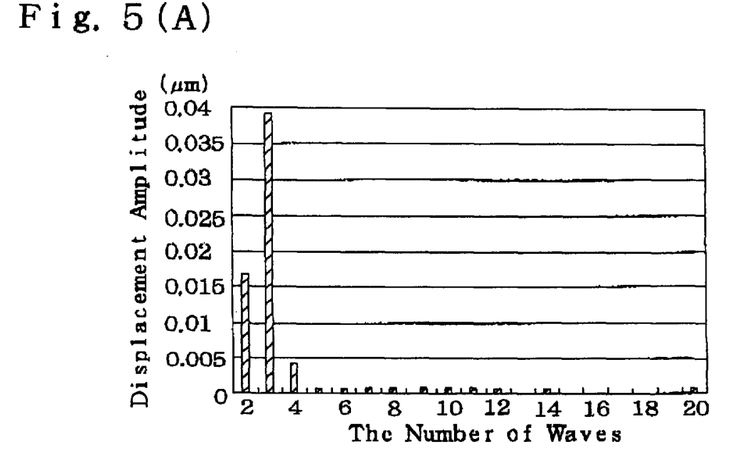
FIG. 5 is a graph to show an example of maturement results according to the surface shape evaluation device for a spherical body of the present invention.
Figure 5B:
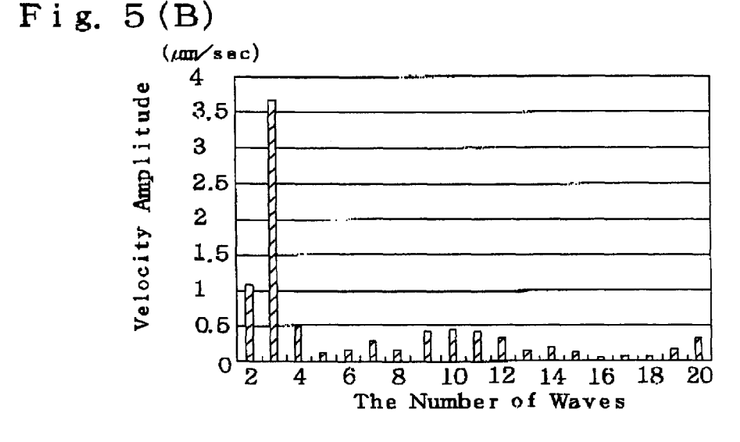
Figure 5C:
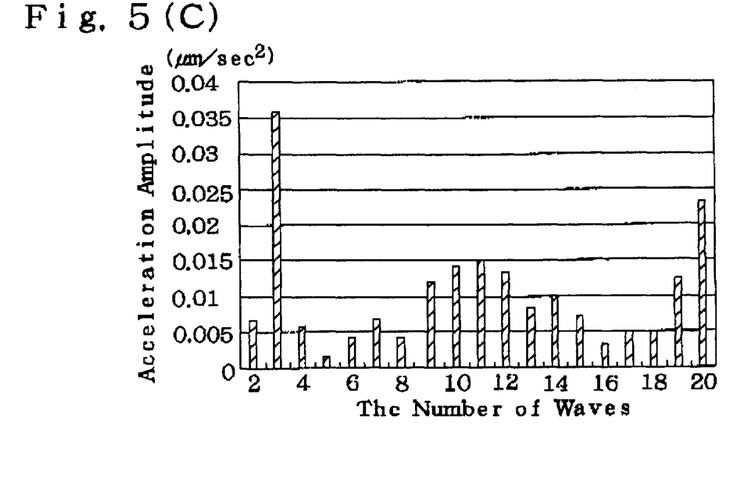

The operation process can be conducted through harmonic analysis. The surface shape evaluation device of the present invention is used to measure the shape of the rolling surface of the same ball 6 to obtain the characteristic values, specifically displacement, velocity, and acceleration. FIGS. 5(A), 5(B), and 5(C) show an example of the displacement amplitude, velocity amplitude, and acceleration amplitude with respect to the number of waves, respectively. Here, the displacement amplitude, velocity amplitude, and acceleration amplitude mean the degree of the displacement due to the vibration detected by the sensor 9, the degree of the velocity of the vibration detected by the sensor 9, and the degree of the acceleration of the vibration detected by the sensor 9. As clear from FIGS. 5(A), 5(B), and 5(C), when the number of waves is five or more, the displacement amplitude is smaller, and it is difficult to evaluate the displacement amplitude. However, the velocity amplitude and acceleration amplitude, particularly the latter can be sufficiently evaluated even when the number of waves is large.

The analysis results from the frequency analyzer 15 are subjected to the operation process at the spectrum computing element 16, and then, the measurement results are output from the display means such as CRT, printer (not shown). The operator evaluates the ball 6, good or not, from the output of the display means. This decision can be automatically conducted. For example, it is possible to set the upper and lower values of the number of waves affecting the acoustic performance and vibration of the ball bearing having the ball 6 incorporated therein as requested by users, such as HDD manufacturers, so that the evaluation of the characteristic values is made within the range set. In this case, waviness only with the even orders of waviness is extracted for evaluation of the characteristic values, for reliable and efficient evaluation leading to performance improvement.

Specifically, the even orders of waviness affects the acoustic performance and vibration of the ball bearing worse than the odd orders of waviness. Conventionally, the evaluation was made without separating the even orders of waviness from the odd orders of waviness, and therefore even if the even orders of waviness was small, the products were judged as defective if the odd orders of waviness was large.

Therefore, the products did not pass as good unless both of the even orders of waviness and the odd orders of waviness were made small. Consequently, the roundness of the rolling surface of the ball 6 had to be made better than necessary, and the cost was unavoidably and excessively increased so as to comply with the demand of the users. On the other hand, with the present invention, only the even orders of waviness which affect the acoustic performance and vibration of the ball bearing substantially worse is extracted for evaluation. In other words, the evaluation for the shape of the rolling surface can be made in good alignment between the vibration and the acoustic performance of the ball bearing. Therefore, there is no need of making the roundness of the rolling surface higher than necessary, the cost to comply with the demand of the users can be made lower.

Accordingly, it is possible at the stage of the ball 6 as it is to judge the performance of the ball bearing on vibration and sound or quality of the device in which the ball bearing is incorporated e.g. HDDs, on resonance characteristics. And, the process condition of the ball 6 and the specification of the ball bearing can be optimized, so that the process time of the ball 6 and the cost thereof can be reduced. According to the present invention, the degree of the waviness of the rolling surface of the ball 6 is in good correspondence with the degree of the vibration produced during operation of the ball bearing having the ball 6 incorporated therein.

Figure 6:
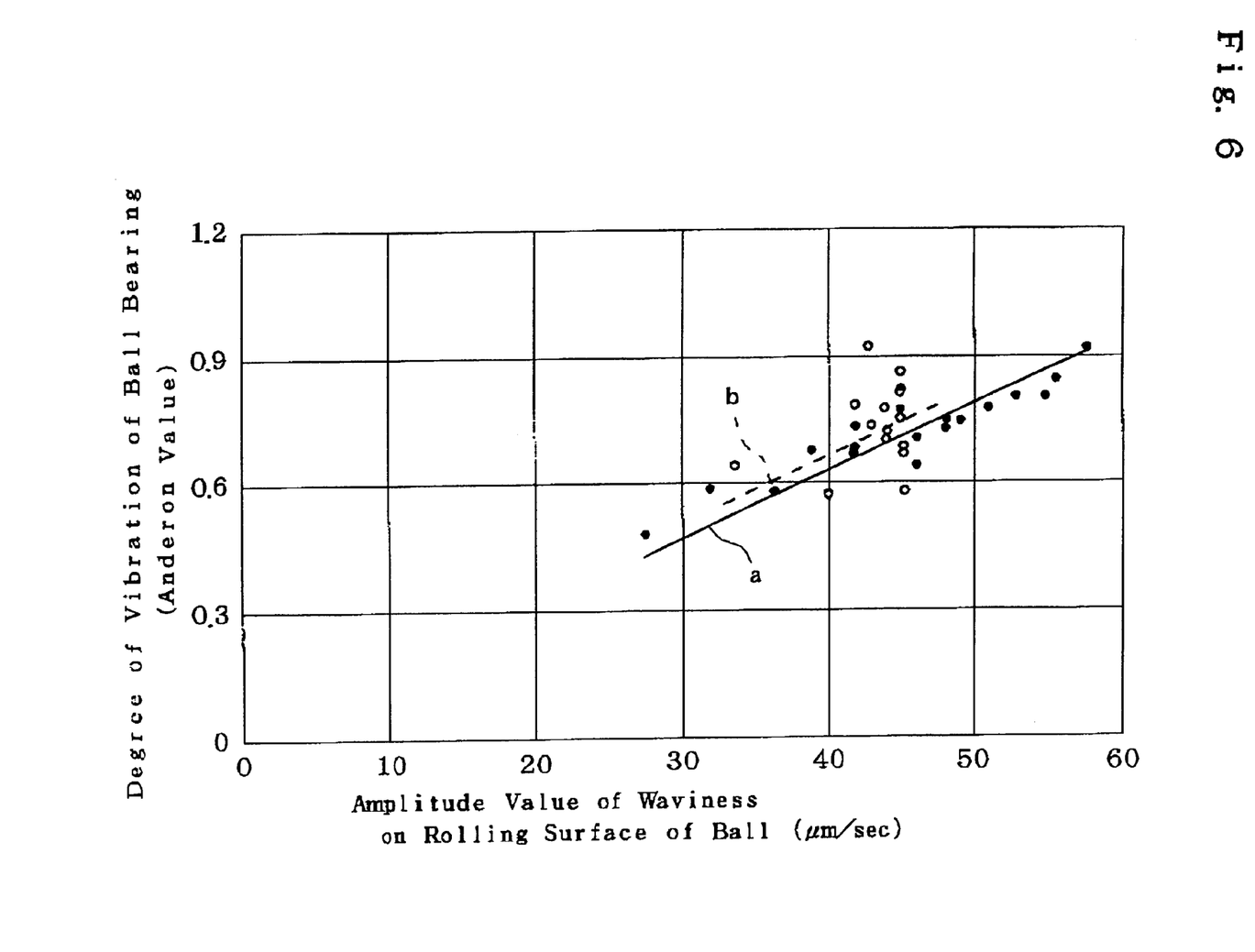
FIG. 6 is a diagram showing a result of the experiment to know the effects of differences in measurement methods on the relation between the degree of waviness on the rolling surface of the ball and the degree of vibration produced during operation of the ball bearing expected from the degree of the waviness.

FIG. 6 shows a result of the experiment the present inventors made on the correspondence, wherein the dimensions of the ball bearing (No. 695) are as follows: inner diameter: 5 mm, outer diameter, 13 mm, width: 4 mm, ball diameter: 2 mm, and the number of balls: 8.

In FIG. 6, the ordinate represents the degree (Anderson Value) of vibration produced during operation of the ball bearing, while the abscissa represents the velocity of the characteristic value of the amplitude of the waviness on the rolling surface of the ball 6. Black circles represent the relation between the amplitude of the waviness of the ball 6 obtained through the evaluation device of the present invention and the degree of the vibration produced during operation of the ball bearing having the ball 6 incorporated therein. White circles represent the relation between the amplitude of the waviness of the ball 6 obtained through a waviness meter conventionally used and the degree of the vibration produced during operation of the ball bearing having the ball 6 incorporated therein. Solid line (a) represents the summary through the least squares method of the experiment results for the present invention as shown by the black circles while dotted line (b) represents the summary through the least square method of the experiment results for the prior art device as shown by the white circles.

As clear from the experiment results shown in FIG. 6, with the surface shape evaluation method and device for a spherical body according to the present invention, the degree of the vibration produced during operation in the ball bearing having the balls 6 incorporated therein can be highly precisely expected by measuring the surface shape of the rolling surface of the ball 6. Specifically, with the comparison between the distributions of the black circles for the solid line (a) and of the white circles for the dotted line (b), dispersion in degree of the vibration produced during operation of the ball bearing, which is expected from the amplitude of waviness on the rolling surface of the ball 6, is smaller in the present invention. The correlation coefficient (r) in the statics of the distributions of the black circles for the solid line (a) and of the white circles for the dotted line (b) are r=0.9 and r=0.5 respectively.

Figure 7:
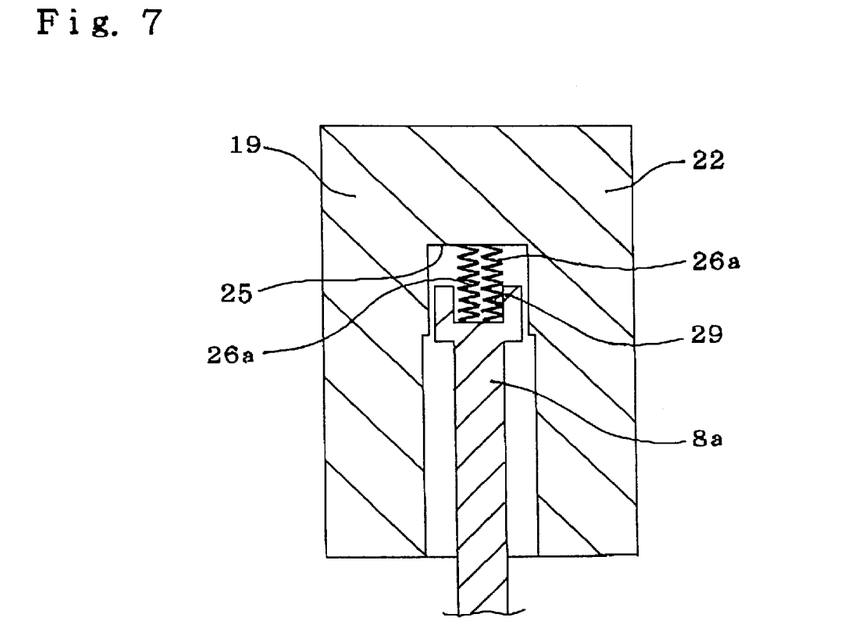
FIG. 7 is a vertical cross sectional view of a second example of the drive apparatus to rotate the ball.
Figure 8:
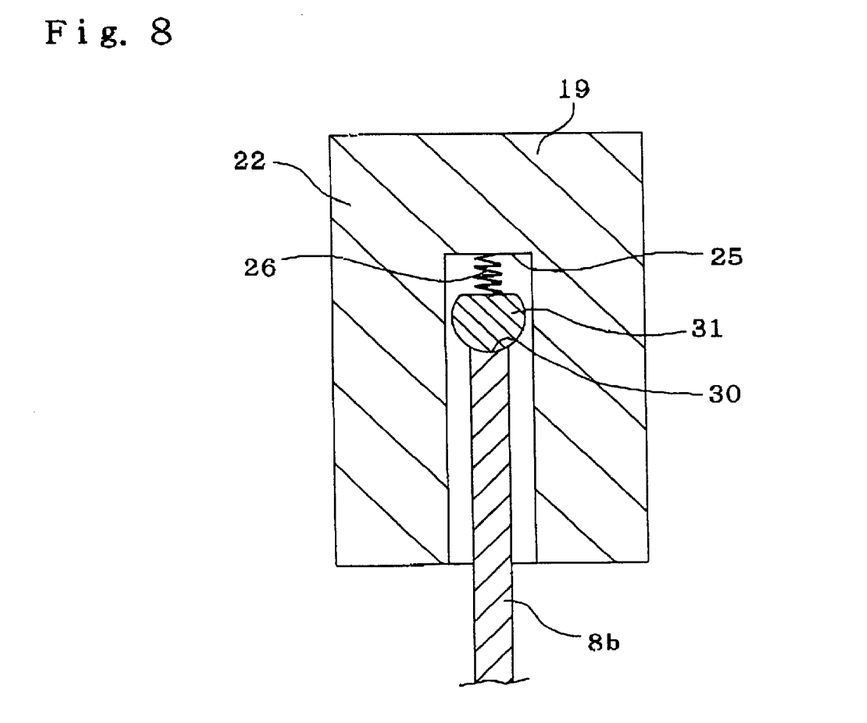
FIG. 8 is a vertical cross sectional view of a third example of the drive apparatus to rotate the ball.

FIGS. 7 and 8 show examples of the drive apparatus portion 19 for second and third examples of the embodiment of the present invention.

In the second example of FIG. 7, the upper end of the drive arm 8a is provided with a receptor portion 29 in a bottomed cylindrical shape with the upper end being open, and compression coil springs 26a are provided between the bottom surface of the receptor portion 29 and the innermost surface of the recess 25 on the lower end of the spindle 22.

In the third example of FIG. 8, the upper end of the drive arm 8b is provided with a spherical recess 30 with which the lower surface of the transmission piece 31 comes into contact in a swinging manner, wherein the transmission piece 31 is formed in a spherical convex surface shape except for the upper end thereof. And compression coil springs 26 are provided between the upper end of the transmission piece 31 and the innermost surface of the recess 25 on the lower end of the spindle 22.

In the second and third examples, only the rotation component of the spindle 22 can be transmitted to the ball 6 (see FIG. 3). The remaining portions in construction and operation are substantially the same to the those of the first example.

Incidentally, for measurement of the waviness at the equator portion o the rolling surface of the ball 6, any non contact type measurement device such as a laser Doppler type vibration measurement device can be used instead of the contact type sensor 9. In this case, the device must be selected such that the measurement portion has a width for measurement range, and the highest peak is detected for waviness.

Although the present invention is described for the radial bearing, but the ball bearing having the ball 6 incorporated therein after measurement of the waviness on the rolling surface according to the present invention can be of the thrust type.

What is claimed is:
1. A surface shape evaluation method for a spherical body having a central point and a surface with a curvature, comprising the steps of:
   providing a support hole having a smaller diameter than the spherical body and having an outer peripheral edge portion to define an opening, providing a curved bearing surface formed on the outer peripheral edge portion of the opening to have a curvature substantially equal to the curvature of the surface of the spherical body, providing a rotation device arm having a centering function to transmit only a rotation component to the spherical body, providing a vibration sensor having a probe with a flat tip end, rotating the spherical body on a predetermined center axis and one the opening, such that one portion in the radial direction of the spherical body comes into contact with the curved bearing surface while the portion opposite to the one portion in the radial direction of the spherical body comes into contact with the tip end of the rotation drive arm, abutting the flat tip end of the probe of the vibration sensor to a surface portion of the spherical body located on a hypothetical flat surface which is orthogonal to the center axis and passes through the central pint of the spherical body to detect the surface shape of the surface portion as vibration amounts, converting the vibration amounts to electric signals, subjecting the electric signals to a sampling process and an adding and averaging process to obtain an average in harmonization with rotation velocity of the spherical body caused by the rotation drive arm, subjecting the average to a frequency analysis process to obtain a result, and evaluating the result as a numerical value representing at least one of the characteristic values of displacement, velocity, and acceleration for judgement to the spherical body.

2. A surface shape evaluation device for a spherical body having a central point and a surface with a curvature, comprising:

a rotation guide tool having a support hole having a smaller diameter than the spherical body and having an outer peripheral edge portion to define an opening, and a curved bearing surface formed on the outer peripheral edge portion of the opening to have a curvature substantially equal to the curvature of the surface of the spherical body, a rotation drive means having a centering function to transmit only a rotation component, while one portion in the radial direction of the spherical body comes into contact with the curved bearing surface, to the portion opposite to the one portion in the radial direction of the spherical body, a vibration sensor having a probe with a flat tip end, such that while rotating the spherical body on a predetermined center axis and on the flat opening, the flat tip end of the probe of the vibration sensor is abutted to a surface portion of the spherical body located on a hypothetical flat surface which is orthogonal to the center axis and passes through the central point of the spherical body to detect the surface shape of the surface portion s vibration amounts, a converting means for converting the vibration amounts to electric signals, a harmonic adder for subjecting the electric signals to a sampling process and an adding and averaging process to obtain an average in harmonization with rotation velocity of the spherical body caused by the rotation drive arm, and a decision means for subjecting the average to a frequency analysis process to obtain a result, and evaluating the result as a numerical value representing at least one of the characteristic values of displacement, velocity, and acceleration for judgement to the spherical body.

* * * * *